ABSTRACT

United States Patent [19]

Sarges

[11] 4,029,731
[45] June 14, 1977

[54] AMINOPHENYLTETRALIN COMPOUNDS

[75] Inventor: Reinhard Sarges, Mystic, Conn.

[73] Assignee: Pfizer Inc., New York, N.Y.

[22] Filed: June 4, 1976

[21] Appl. No.: 692,764

Related U.S. Application Data

[60] Division of Ser. No. 521,451, Nov. 6, 1974, abandoned, which is a continuation of Ser. No. 292,526, Sept. 27, 1972, abandoned.

[52] U.S. Cl. .................... 424/316; 260/501.1; 260/501.21; 260/576; 424/330
[51] Int. Cl.² ............... A01N 9/20; A01N 9/24; C07C 87/64
[58] Field of Search .......... 260/501.1, 501.21, 576; 424/316, 330

[56] References Cited

UNITED STATES PATENTS 3,347,870  10/1967  Rutschmann et al. ......... 260/576 X

Primary Examiner—Robert V. Hines
Attorney, Agent, or Firm—Connolly and Hutz

[57] ABSTRACT

A series of novel 4-phenyl-1,2,3,4-tetrahydro-1-naphthylamines, including their pharmaceutically acceptable acid addition salts and their cis- and trans-isomers, have been prepared. The trans-isomers are useful in the field of mental health as antidepressant agents and/or as psychomotor stimulants. The trans-isomer of N-methyl-4-phenyl-1,2,3,4-tetrahydro-1-naphthylamine represents a preferred embodiment.

5 Claims, No Drawings

AMINOPHENYLTETRALIN COMPOUNDS

CROSS REFERENCE TO RELATED APPLICATIONS

This application is a division of application Ser. No. 521,451 filed Nov. 6, 1974 now abandoned which is a continuation of application Ser. No. 292,526 filed Sept. 27, 1972 and now abandoned.

BACKGROUND OF THE INVENTION

This invention relates to new and useful 1-amino-4-phenyltetralin compounds. More particularly, it is concerned with certain novel 4-phenyl-1,2,3,4-tetrahydro-1-naphthylamines and their pharmaceutically acceptable acid addition salts, which are of value in therapy in view of their unique psychotherapeutic properties.

In the past, various attempts have been made by numerous investigators in this particular field of therapy to obtain new and improved agents for the treatment of mental depression and apathy. In some instances, these efforts have involved the synthesis and testing of various compounds having a benzocycloalkane-type structure. For example, C. F. Huebner in U.S. Pat. No. 3,201,470 discloses certain 1-propargylaminotetralins that are useful as stimulants or as psychic energizing agents due to their ability to act as monoamine oxidase inhibitors. However, little is known about the effect of other heretofore unavailable 1-aminobenzocycloalkanes in this area, particularly with respect to their effect on mental health and so on.

SUMMARY OF THE INVENTION

In accordance with the present invention, it has now been surprisingly found that certain novel 1-amino-4-phenyltetralins are extremely useful when employed in the field of drug therapy as psychotropic agents even though they do not function as monoamine oxidase inhibitors. The novel compounds of this invention are all selected from the group consisting of 1-amino-4-phenyltetraline bases of the formula:

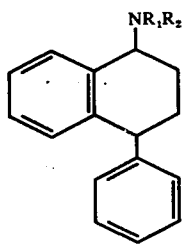

and the pharmaceutically acceptable salts thereof, wherein $R_1$ is a member selected from the group consisting of hydrogen and alkyl having from one to three carbon atoms, and $R_2$ is a member selected from the group consisting of hydrogen, alkyl having from one to three carbon atoms and cycloalkyl having from three to six carbon atoms, said $R_2$ only being cycloalkyl when $R_1$ is hydrogen. The trans-isomers of these novel compounds are all useful in the treatment of mentally depressed states in view of their antidepressant properties and psychomotor stimulant activity.

Of especial interest in this connection are such typical and preferred member compounds of the invention as trans-dl-N-methyl-4-phenyl-1,2,3,4-tetrahydro-1-naphthylamine, trans-d-N-methyl-4-phenyl-1,2,3,4-tetrahydro-1-naphthylamine, trans-dl-N-ethyl-4-phenyl-1,2,3,4-tetrahydro-1-naphthylamine, trans-dl-N-isopropyl-4-phenyl-1,2,3,4-tetrahydro-1naphthylamine, trans-dl-N-cyclopropyl-4-phenyl-1,2,3,4-tetrahydro-1-naphthylamine, trans-dl-dl-N,N-dimethyl-4-phenyl-1,2,3,4-tetrahydro-1-naphthylamine and trans-dl-4-phenyl-1,2,3,4-tetrahydro-1-naphthylamine and their hydrochloride acid addition salts. These particular compounds all exhibit a markedly high degree of antidepressant activity in addition to their aforesaid behavioral and psychomotor stimulation.

DETAILED DESCRIPTION OF THE INVENTION

In accordance with the principal process employed for preparing the novel compounds of this invention, 4-phenyltetralone is reacted in the presence of titanium tetrachloride with an appropriate primary or secondary amine of the formula $R_1R_2NH$, wherein $R_1$ and $R_2$ are each as previously defined, to give an intermediate Schiff base (ketimine), or enamine, as the case my be, which is then reduced by means of catalytic hydrogenation or with a complex metal hydride to yield the desired final product. Preferred reaction conditions, particularly in connection with the reduction of the aforesaid ketimine compound (i.e., intermediate Schiff base formed from the primary amine), include the use of lithium aluminum or diborane in an ether-type organic solvent, or the use of sodium or potassium borohydride in a lower alkanol such as methanol or ethanol, at a temperature ranging from room temperature up to the reflux point of the reaction mixture. In this way, 4-phenyltetralone is converted via N-methyl-4-phenyl-3,4-dihydro-1-naphthylamine to dl-N-methyl-4-phenyl-1,2,3,4-tetrahydro-1-naphthylamine.

Alternatively, 4-phenyltetralone can simply be converted to its oxime(via hydroxylamine) and the latter intermediate reduced with hydrogen in the presence of a palladium-on-carbon catalyst to give the resultant primary amine, viz., 4-phenyl-1,2,3,4-tetrahydro-1-naphthylamine. The latter compound can also be obtained from the same starting material by reduction of the corresponding phenylhydrazone derivative using zinc dust and an acid such as acetic acid. Conversion of the aforesaid primary amine to a compound like dl-N,N-dimethyl-4-phenyl-1,2,3,4-tetrahydro-1-naphthylamine can then be accomplished by treatment with at least a dimolar excess of an alkylating agent such as methyl iodide or with an excess of formaldehyde in a formic acid medium, dl-N-Methyl-4-phenyl-1,2,3,4-tetrahydro-1-naphthylamine is also converted to dl-N,N-dimethyl-4-phenyl-1,2,3,4-tetrahydro-1-naphthylamine in this manner.

The compounds produced by the various processes hereinbefore described exist in cis- and trans-isomeric forms, and these are both contemplated as being within the purview of the present invention. For instance, the cis/trans-isomeric mixtures directly obtained on synthesis per se exhibit therapeutic properties of the same type possessed by these novel compounds, although it is to be clearly understood that biological activity primarily resides in the trans form. The latter is obtained by fractionally crystallizing the pure isomeric base in salt form from a solution of the corresponding isomeric admixture with the cis-isomer, preferably employing DL- mandelic acid and an alcohol-ether solvent medium for these purposes. When D-(−)-mandelic acid is substituted for DL-mandelic acid in this reaction, the corresponding d- and l-optical isomers of the trans compound are ultimately obtained.

More particularly, resolution of the racemic 1-amino-4-phenyltetralin compounds of this invention is achieved by using D-(—)-mandelic acid as the initial resolving agent therefor in a lower alkanoic solvent medium (e.g., methanol), whereby the less soluble diastereoisomeric salt form is subsequently isolated therefrom as a crystalline precipitate. Treatment of the remaining alcoholic mother liquors with N-acetyl-L-tyrosine then yields the corresponding diasteroisomeric salt of the other optical isomer. In this way, a compound such as trans-dl-N-methyl-4-phenyl-1,2,3,4-tetrahydro-1-naphthylamine is eventually separated into its respective d- and l-optical antipodes.

The pharmaceutically acceptable acid addition salts of the 1-amino-4-phenyltetralin base compounds of this invention are prepared by simply treating the aformentioned organic bases with various mineral and organic acids which form non-toxic acid addition salts having pharmacologically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts. For instance, the salt-formation step may be carried out by using a substantially equimolar amount of the appropriate acid in an aqueous solvent medium or in a suitable organic solvent such as methanol or ethanol. Upon careful evaporation of the solvent, the solid salt product is readily obtained.

As previously indicated, the 1-amino-4-phenyltetralin compounds of this invention (in the form of their trans-isomers) are all readily adapted to therapeutic use as psychotropic agents, particularly in view of their potent antidepressant and psychomotor stimulant properties. For instance, trans-d-N-methyl-4-phenyl-1,2,3,4-tetrahydro-1-naphthylamine hydrochloride, a typical and preferred agent of the present invention, has been found to exhibit marked antidepressant and psychomotor stimulant activity in rats when given by the intraperitoneal route of administration at levels ranging from 3.2 mg./kg. to 32 mg./kg., respectively, without showing any substantial signs of toxic side effects. The other compounds of this invention also cause similar results. Furthermore, all the herein described trans-isomers of this invention can be administered as psychotropic agents by either the oral or parenteral routes of administration, for the present purposes at hand, without causing any significant untoward pharmacological side effects to occur in the subject to whom they are so administered. In general, these psychotropic compounds are normally administered in dosages ranging from about 0.3 mg., to about 10 mg. per kg. of body weight per day, although variations will necessarily occur depending upon the weight and conditions of the subject being treated and the particular route of administration chosen.

In connection with the use of the 1-amino-4-phenyltetralin compounds of this invention for the treatment of depressed subjects, it is to be noted that these compounds may be administered either along or in combination with pharmaceutically acceptable carriers by either of the routes previously indicated, and that such administration can be carried out in both single and multiple dosages. More particularly, the novel compounds of this invention can be administered in a wide variety of different dosage forms, i.e., they may be combined with various pharmaceutically-acceptable inert carriers in the form of tablets, capsules, lozenges, troches, hand candies, powders, sprays, aqueous suspension, injectable solutions, elixirs, syrups, and the like. Such carriers include solid diluents or fillers sterile aqueous media and various non-toxic organic solvents, etc. Moreover, such oral pharmaceutical formulations can be suitably sweetened and/or flavored by means of various agents of the type commonly employed for just purposes. In general, the therapeutically useful compounds of this invention are present is such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

For purposes of parenteral administration, solutions of these particular 1-amino-4-phenyltetralins in seasame or peanut oil or in aqueous propylene glycol or N,N-dimethylformamide may be employed, as well as sterile aqueous solutions of the corresponding water-soluble, non-toxic mineral and organic acid addition salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

The activity of the compounds of the present invention as antidepressants is determined by a study of their ability to supress norepinephrine uptake into both rat heart and rat brain (in vivo), together with a determination of their ability to bring about a reversal of reserpine hypothermia in mice. In this way, trans-d-N-methyl-4-phenyl-1,2,3,4-tetrahydro-1-naphthylamine hydrochloride was found to be roughly equivalent to both imipramine and desmethylimipramine as regards drug potency in this connection.

On the other hand, the activity of the compounds of the present invention, as psychomotor stimulants, is based on a variety of tests, including (1) a study of their motor activity in mice and (2) a measurement of their ability to influence the loss of avoidance behavior in rats trained on a non-discriminated (Sidman) avoidance schedule. In this way, trans-d-N-methyl-4-phenyl-1,2,3,4-tetrahydro-1-naphthylamine (as the hydrochloride salt) was found to be comparable in potency to methylphenidate as a psychomotor stimulant, possessing both a rapid onset of action and a long duration of motor stimulant activity.

EXAMPLE I

In a dry 5-liter three-necked, round-bottomed flask equipped with dropping funnel, mechanical stirrer and thermometer, there were placed 133 g. (0.6 mole) of 4-phenyltetralone [prepared from benzophenone according to procedures described in the *Journal of the American Chemical Society*, Vol. 69, p. 77 (1947); ibid., Vol. 70, p. 1071 (1948); ibid., Vol. 72, p. 501 (1950); ibid., Vol. 76, p. 1642 (1954)] dissolved in 2 liters of benzene. Stirring commenced and the solution was then cooled to 50° C., at which point 111.6 g. (3.6 mole) of liquid methylamine were slowly added thereto, followed by the dropwise addition of 33 ml. (0.3 mole) of titanium tetrachloride in 500 ml. of benzene at 0°-5° C. The latter step was carried out during the course of a 30-minute period at such a rate that the temperature never exceeded 5° C. The resulting mixture was then allowed to warm slowly to room temperature (~25° C.), stirred continuously thereafter at said temperature for a period of 4 hours and finally, allowed to stand overnight (a period of approximately 16 hours) at ambient temperatures without any further stirring being necessary. At this point, the spent reaction mixture was filtered while under a dry nitrogen atmosphere and the solids that had been collected on the filter funnel in this manner were thereafter washed with a fresh portion of benzene. The combined benzene filtrate and washings were then evaporated to near dryness while under reduced pressure to give 135.1 g. (95%) of oily ketimine, i.e., an almost quantitative yield of N-methyl-4-phenyl-3,4-dihydro-1(2H)-naphthalenone imine (m.p. 69°-70° C. after crystallization from n-hexane). The oily product was used as such in the next reaction step.

To a solution of the above ketimine (135.1 g., 0.75 mole) in 800 ml. of chilled methanol, cooled in an ice bath, there were slowly introduced 21.7 g. (0.75 mole) of sodium borohydride added in several small portions during the course of a 30-minute period, with the temperature of the mixture always being maintained below 60° C. Upon completion of this step, the resulting mixture was stirred at room temperature for a period of approximately 20 minutes (until all gas evolution had ceased) and was thereafter concentrated in vacuo to afford a solid residue that was subsequently triturated with 500 ml. of water. The latter aqueous phase (i.e., the suspension) was then extracted three times with fresh 500 ml. portions of diethyl ether, and the combined ethereal extracts were subsequently dried over anhydrous magnesium sulfate and filtered. Evaporation of the filtrate under reduced pressure then gave 135.1 g. (99%) of dl-N-methyl-4-phenyl-1,2,3,4-tetrahydro-1-naphthylamine in the form of a cis/trans mixture of isomers as the residual oil.

EXAMPLE II

An ethereal solution of the cis/trans isomer mixture of Example I (i.e., cis/trans-dl-N-methyl-4-phenyl-1,2,3,4-tetrahydro-1-naphthylamine that had been derived from a 5.0 g. portion of the ketimine) was treated with an excess of dry hydrogen chloride gas to give a crystalline precipitate of the corresponding hydrochloride salts. The latter material (i.e., the crystalline isomeric salt mixture) was promptly collected by means of suction filtration, washed on the filter funnel with some diethyl ether and then dissolved in hot water to give an aqueous solution. On cooling the latter to room temperature (~25° C.), there were obtained crystals of the less soluble cis-isomer of dl-N-methyl-4-phenyl-1,2,3,4-tetrahydro-1-naphthylamine (as the hydrochloride) and these were then further purified by means of recrystallization from an ethanol-diethyl ether solvent system. In this way, there was ultimately obtained a 2.3 g. (40%) yield of pure crystalline cis-dl-N-methyl-4-phenyl-1,2,3,4-tetrahydro-1-naphthylamine hydrochloride, m.p. 241°-242° C.

Anal. Calcd. for $C_{17}H_{19}N \cdot HCL$: C, 74.56; H, 7.36; N, 5.11. Found: C, 74.44; H, 7.46; N, 5.11.

The aqueous mother liquor obtained above after removal of the cis-isomer then gave, on cooling in an ice bath, the corresponding trans form of dl-N-methyl-4-phenyl-1,2,3,4-tetrahydro-1-naphthylamine. After recrystallization from methanol-diethyl ether, the yield of pure trans-dl-N-methyl-4-phenyl-1,2,3,4-tetrahydro-1-naphthylamine hydrochloride amounted to 1.9 g. (33%). The crystalline product melted at 224°-225° C.

Anal. Calcd. for $C_{17}H_{19}N \cdot HCl$: C, 74.56; H, 7.36; N, 5.11. Found: C, 74.42; H, 7.30; N, 4.99.

EXAMPLE III

A solution consisting of 135.1 g. (0.57 mole) of the cis/trans isomer mixture of dl-N-methyl-4-phenyl-1,2,3,4-tetrahydro-1-naphthylamine (prepared as described in Example I) dissolved in 250 ml. of methanol was treated with 43.3 g. (0.285 mole) of D-(−)-mandelic acid (i.e., l-mandelic acid) and the resulting mixture was heated on a steam bath until a clear solution was obtained. After cooling to room temperature (~25° C.), 500 ml. of diethyl ether were added and the mixture was then allowed to stand at room temperature for a period of 1 hour. The precipitated solids which formed at this point were then collected on a filter funnel by means of suction filtration, washed well with diethyl ether and recrystallized twice from methanol to give 38.0 g. of pure trans-d-N-methyl-4-phenyl-1,2,3,4-tetrahydro-1-naphthylamine l-mandelate, m.p. 129°-130° C. This particular diastereoisomer was then converted to the free organic base compound by treatment with 250 ml. of 1N aqueous sodium hydroxide and subsequently isolated as the hydrochloride salt (m.p. 224°-226° C.) in accordance with standard procedure. After recrystallization from methanol-diethyl ether (1:1 by volume), there were ultimately obtained 21.8 g. (15%) of trans-d-N-methyl-4-phenyl-1,2,3,4-tetrahydro-1-naphthylamine as the hydrochloride, m.p. 229°-230° C.,; $[\alpha]_D^{24°}$ +41° (c=1 in methanol). This isomer has been assigned the 1R, 4S configuration.

Anal. Calcd. for $C_{17}H_{19}N \cdot HCl$: C, 74.56; H, 7.36; N, 5.11. Found: C, 74.73; H, 7.36; N, 5.09.

The mother liquor of the D-(−)mandelate (or l-mandelate) obtained above after first being converted to the free base compound was then treated with 0.33 equivalents (this was based on the original amount of dl-amine starting material) of N-acetyl-L-tyrosine in a methanol-diethyl ether (1:4 by volume) solvent system. This resulted in the formation of trans-l-N-methyl-4-phenyl-1,2,3,4-tetrahydro-1-naphthylamine N-acetyl-L-tyrosinate (m.p. 228°-230° C.) as a precipitate. After conversion to the hydrochloride salt in the usual manner as before, there was finally obtained pure trans-l-N-methyl-4-phenyl-1,2,3,4-tetrahydro-1-naphthylamine hydrochloride, m.p. 229°–230° C.; $[\alpha]_D^{24°}$ —41° (c=1, methanol). This particular isomer has been assigned the 1S, 4R configuration.

Anal. Calcd. for $C_{17}H_{19}N \cdot HCl$: C, 74.56; H, 7.36; N, 5.11. Found: C, 74.73; H, 7.31; H, 4.99.

EXAMPLE IV

The procedure described in Example III was followed except that the cis/trans isomer mixture of dl-N-methyl-4-phenyl-1,2,3,4-tetrahydro-1-naphthylamine was treated with an equivalent amount of DL-mandelic acid (rather than with 0.5 equivalents of D-(—)-mandelic acid) in a methanol-diethyl ether (1:10 by volume) solvent system. In this particular case, the trans-isomer of the corresponding DL-mandelate crystallized out preferentially and there was ultimately obtained a substantial yield of pure crystalline trans-dl-N-methyl-4-phenyl-1,2,3,4-tetrahydro-1-naphthylamine DL-mandelate, m.p. 104°–108° C. Conversion to the hydrochloride salt in the usual manner as before (i.e., via the free organic base intermediate) then gave pure trans-dl-N-methyl-4-phenyl-1,2,3,4-tetrahydro-1-naphthylamine hydrochloride (m.p. 224°–225° C.) in a 31% yield. This product was identical in every respect with the trans-isomer obtained in Example II.

In like manner, the mother liquor containing the cis-mandelate ultimately gave (after conversion to the hydrochloride salt) the pure cis-isomer of dl-N-methyl-4-phenyl-1,2,3,4-tetrahydro-1-naphthylamine hydrochloride (m.p. 241°–242° C.) in a 28% yield.

EXAMPLE V

The procedure described in Example I was repeated except that ethylamine was employed as the starting material of choice instead of methylamine. In this particular case, using the same molar proportions as before, 4-phenyltetralone (i.e., 4-phenyl-3,4-dihydro-1(2H)-naphthalenone) was converted via N-ethyl-4-phenyl-3,4-dihydro-1(2H)-naphthalenone imine to dl-N-ethyl-4-phenyl-1,2,3,4-tetrahydro-1-naphthylamine in the form of a cis/trans mixture of isomers. Conversion to the corresponding hydrochloride salts in the manner of the preceding Example then separately gave pure cis-dl-N-ethyl-4-phenyl-1,2,3,4-tetrahydro-1-naphthylamine hydrochloride and trans-dl-N-ethyl-4-phenyl-1,2,3,4-tetrahydro-1-naphthylamine hydrochloride, respectively. The cis-isomer melted at 261°–263° C., while the trans form of the compound melted at 224°–225° C.

Anal. Calcd. for $C_{17}H_{21}N \cdot HCl$: C, 75.12; H, 7.71; N, 4.86. Found: (cis); C, 74.88; H, 7.63; N, 4.85. (trans): C, 75.00; H, 7.78; N, 5.11.

EXAMPLE VI

The procedure described in Example I was repeated except that isopropylamine was employed as the starting material of choice instead of methylamine. In this particular case, using the same molar proportions as before, 4-phenyltetralone was converted via N-isopropyl-4-phenyl-3,4-dihydro-1(2H)-naphthalenone imine to dl-N-isopropyl-4-phenyl-1,2,3,4-tetrahydro-1-naphthylamine in the form of a cis/trans mixture of isomers. Conversion to the corresponding hydrochloride salts in the manner of Example II, followed by fractional crystallization of the isomers then separately gave pure cis-dl-N-isopropyl-4-phenyl-1,2,3,4-tetrahydro-1-naphthylamine hydrochloride and pure trans-dl-N-isopropyl-4-phenyl-1,2,3,4-tetrahydro-1-naphthylamine hydrochloride, respectively. The cis-isomer melted at 228°–229° C., while the trans form of the compound melted at 283°–284° C.

Anal. Calcd. for $C_{19}H_{23}N \cdot HCl$: C, 75.61; H, 8.01; N, 4.64. Found: (cis): C, 75.43; H, 7.97; N, 4.64. (trans): C, 75.39; H, 7.96; N, 4.53.

EXAMPLE VII

The procedure described in Example I was repeated except that cyclopropylamine was employed as the starting material of choice instead of methylamine. In this particular case, using the same molar propertions as before, 4-phenyltetralone was converted via N-cyclopropyl-4-phenyl-3,4-dihydro-1(2H)-naphthalenone imine to dl-N-cyclopropyl-4-phenyl-1,2,3,4-tetrahydro-1-naphthylamine in the form of a cis/trans mixture of isomers. Conversion to the corresponding hydrochloride salts in the manner of Example IV then separately gave pure cis-dl-N-cyclopropyl-4-phenyl-1,2,3,4-tetrahydro-1-naphthylamine hydrochloride and pure trans-dl-N-cyclopropyl-4-phenyl-1,2,3,4-tetrahydro-1-naphthylamine hydrochloride, respectively. The cis-isomer melted at 223°–224° C., while the trans form of the compound melted at 218°–220° C.

Anal. Calcd. for $C_{19}H_{21}N \cdot HCl$: C, 76.10; H, 7.39; N, 4.67. Found: (cis): C, 75.85; H, 7.36; N, 4.68. (trans): C, 75.84; H, 7.31; N, 4.67.

EXAMPLE VIII

A solution consisting of 390 mg. (0.00164 mole) of trans-dl-N-methyl-4-phenyl-1,2,3,4-tetrahydro-1-naphthylamine (obtained by treatment of the corresponding hydrochloride in Example IV with 10% aqueous sodium bicarbonate) dissolved in 5 ml. of formic acid was mixed with 5 ml. of 37% aqueous formaldehyde and the resulting mixture heated on the steam bath for a period of one hour. After concentrating the resulting reaction mixture in vacuo, the residual free base compound was converted to the hydrochloride salt in the usual manner and recrystallized as such from a methanol-diethyl ether (1:4 by volume) solvent system to give 0.5 g. (84%) of pure trans-dl-N,N-dimethyl-4-phenyl-1,2,3,4-tetrahydro-1-naphthylamine hydrochloride, m.p. 229°–230° C.

Anal. Calcd. for $C_{18}H_{21}N \cdot HCl$: C, 75.12; H, 7.71; N, 4.86. Found: C, 74.87; H, 7.80; N, 4.71.

In like manner, cis-dl-N-methyl-4-phenyl-1,2,3,4-tetrahydro-1-naphthylamine (obtained via treatment of the corresponding hydrochloride in Example IV with 10% aqueous sodium bicarbonate) gave pure cis-dl-N,N-dimethyl-4-phenyl-1,2,3,4-tetrahydro-1-naphthylamine hydrochloride, m.p. 192°–194° C.

Anal. Calcd. for $C_{18}H_{21}N \cdot HCl$: C, 75.12; H, 7.71; N, 4.86. Found: C, 75.18; H, 7.66; N, 4.74.

EXAMPLE IX

To a well-stirred solution consisting of 4.9 g. (0.022 mole) of 4-phenyl-1-tetralone dissolved in 80 ml. of ethanol, there were successively added 16 ml. of water and 1.72 g. (0.025 mole) of hydroxylamine hydrochloride, followed by 54.0 g. (0.11 mole) of sodium hydroxide divided into small portions. The resulting mixture was then heated on a steam bath for 45 minutes, the concentrate cooled to room temperature (~25° C.) and the residual material subsequently dissolved in 100 ml. of chloroform. After washing the chloroform solution thoroughly with 100 ml. of 1N hydrochloric acid, the aqueous layer separated and was re-extracted with 100 ml. of fresh chloroform. The combined organic layers were then dried over anhydrous magnesium sulfate, filtered and the resulting filtrate subsequently concentrated in vacuo to afford a residual product that later crystallized from chloroform-hexane to yield 3.58 g. (69%) of the desired oxime, m.p. 114°–115° C.

Anal. Calcd. for $C_{15}H_{15}NO$: C, 80.98; H, 6.37; N, 5.90. Found: C, 80.74; H, 6.48; N, 5.90.

Hydrogenation of the above oxime was then accomplished by dissolving 2.0 g. (0.0084 mole) of same in ethanol and using 10% palladium-on-carbon as catalyst with 50 p.s.i. pressure of hydrogen at 25° C. After a period of two hours, the reaction ceased (as evidenced by no more hydrogen up-take), the mixture was filtered and the resulting filtrate was evaporated to dryness while under reduced pressure. Conversion of the residual amine material to the hydrochloride salt in the usual manner, followed by fractional crystallization of the isomers from a methanol-diethyl ether (1:1 by volume) solvent system then gave 0.7 g. (32%) of trans-4-phenyl-1,2,3,4-tetrahydro-1-naphthylamine hydrochloride (m.p. 301°–302° C.) and 1.4 g. (64%) of cis-dl-4-phenyl-1,2,3,4-tetrahydro-1-naphthylamine hydrochloride (m.p. 279°–281° C.).

Anal. Calcd. for $C_{16}H_{17}N\cdot HCl$: C, 73.97; H, 6.99; N, 5.39. Found: (cis): C, 73.96; H, 7.03; N, 5.37. (trans): C, 73.82; H, 6.85; N, 5.31.

EXAMPLE X

Ten parts by weight of trans-d-N-methyl-4-phenyl-1,2,3,4-tetrahydro-1-naphthylamine hydrochloride in 50 parts by volume of water is neutralized with 10N aqueous sodium hydroxide solution. Extraction of the resulting aqueous solution with several portions of methylene chloride, followed by separation of the organic layer and its subsequent concentration under reduced pressure then affords pure trans-d-N-methyl-4-phenyl-1,2,3,4-tetrahydro-1-naphthylamine as a free organic base compound.

In like manner, when any of the other 1-amino-4-phenyltetralin salts of this invention, like trans-dl-N,N-dimethyl-4-phenyl-1,2,3,4-tetrahydro-1-naphthylamine hydrochloride of Example VIII, for instance, are each individually subjected to this very same reaction procedure, the corresponding free organic base coumpound is always the final product thus obtained.

EXAMPLE XI

The following 1-amino-4-phenyltetralines are ultimately obtained in the form of their trans-isomers by employing the procedures described in the previous examples, starting from readily available organic materials in each instance:

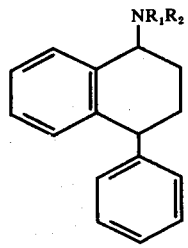

| $R_1$ | $R_2$ |
|---|---|
| hydrogen | n-propyl |
| hydrogen | cyclohexyl |
| methyl | ethyl |
| methyl | isopropyl |
| ethyl | ethyl |
| ethyl | isopropyl |
| isopropyl | isopropyl |
| n-propyl | n-propyl |
| hydrogen | cyclobutyl |
| hydrogen | cyclopentyl |

EXAMPLE XII

The non-toxic hydrohalide acid addition salts of each of the previously reported 1-amino-4-phenyltetralin base compounds of this invention, such as the corresponding novel hydrochloride, hydrobromide and hydriodide salts, are each individually prepared by first dissolving the respective organic base compound in absolute ether followed by the introduction of the appropriate hydrohalide gas in to the reaction solution until saturation of same is complete with respect to said gas, whereupon the desired acid addition salt soon precipitates from said solution. In this way, 5.0 g. of trans-d-N-methyl-4-phenyl-1,2,3,4-tetrahydro-1-naphthylamine, obtained as a free base product in Example X, is converted via dry hydrogen bromide gas to the corresponding hydrobromide acid addition salt in substantially quantitative yield.

EXAMPLE XIII

The nitrate, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts of each of the aforementioned 1-amino-4-phenyltetraline base compounds reported previously are each prepared by dissolving the proper molar amounts of the respective acid and base in separate portions of ethanol and then mixing the two solutions together, followed by the addition of diethyl ether to the resultant mixture in order to effect precipitation of the desired acid addition therefrom. In this manner, equimolar amounts of trans-dl-N,N-dimethyl-4-phenyl-1,2,3,4-tetrahydro-1-naphthylamine and concentrated sulfuric acid react to afford the corresponding sulfuric acid addition salt. In like manner, each of the other salts is prepared.

EXAMPLE XIV

A dry solid pharmaceutical composition is prepared by blending the following materials together in the proportions by weight specified below:

| | |
|---|---|
| Trans-d-N-Methyl-4-phenyl-1,2,3,4-tetrahydro-1-naphthylamine hydrochloride | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 100 mg. of the active ingredient. Other tablets are also prepared in a similar fashion containing 5, 10, 25 and 50 mg. of the active ingredient, respectively, by using 50 the appropriate amount of the 1-amino-4-phenyltetralin salt in each case.

EXAMPLE XV

A dry solid pharmaceutical composition is prepared by combining the following materials together in the proportions by weight indicated below:

| | |
|---|---|
| Trans-dl-N-Methyl-4-phenyl-1,2,3,4-tetrahydro-1-naphthylaminehydrochloride | 50 |
| Calcium carbonate | 20 |
| Polyethylene glycol, average molecular weight, 4000 | 30 |

The dried solid mixture so prepared is then thoroughly agitated so as to obtain a powdered product that is completely uniform in every respect. Soft elastic and hard-filled gelatin capsule containing this pharmaceutical composition are then prepared, employing a sufficient quantity of material in each instance so as to provide each capsule with 50 mg. of the active ingredient.

EXAMPLE XVI

Seven circular acetophotometers, each 39 cm. in diameter and each containing six photocell units, were used to independently study the effects of trans-dl-N-methyl-4-phenyl-1,2,3,4-tetrahydro-1-naphthylamine hydrochloride, trans-d-N-methyl-4-phenyl-1,2,3,4-tetrahydro-1-naphthylamime hydrochloride and its corresponding laevortatory isomer, d-amphetamine sulfate, methylphenidate, desmethylimipramine and protriptyline, respectively, on spontaneous motor activity in mice. A total of seven mice was employed at each dose level tested (viz., at 0.32, 1.0, 3.2, 10 and 32 mg./kg., i.p., respectively) and these mice were separated one to an activity cage. After an initial one-half hour exposure period (for acclimation purposes), each animal in the cage was treated with a sample of the drug intraperitoneally and immediately thereafter returned to said cage, with activity counts every one-half hour being recorded from that point on.

Under these conditions, it was found that trans-d-N-methyl-4-phenyl-1,2,3,4-tetrahydro-1-naphthylamine hydrochloride at 10 mg/kg.(i.p.) markedly elevated the activity counts at periods of 30-60 minutes after treatment, with the effect being more pronounced than that of d-amphetamine sulfate at 3.2 mg./kg. and surpassing even that of methylphenidate at 10 mg./kg. On the other hand, trans-dl-N-methyl-4-phenyl-1,2,3,4-tetrahydro-1-naphthylamine hydrochloride was found somewhat less potent than the aforesaid dextrorotatory isomer, while the laevo form gave little evidence of a stimulant effect even when tested at 10 and 32 mg./kg. (i.p.), respectively. Moreover, desmethylimipramine and protriptlyine both failed to elicit any hyperactive response whatsoever when tested under these same conditions.

Finally, a study of time course data after active doses clearly shows that trans-dl-N-methyl-4-phenyl-1,2,3,4-tetrahydro-1-naphthylamine hydrochloride was especially long-lived after 32 mg./kg., while the corresponding dextrorotatory isomer at 10 mg./kg. seemed even more prolonged in its effect than did that of d-amphetamine sulfate at 3.2 mg./kg., respectively.

EXAMPLE XVII

Eight mature male rats were trained in Lehigh Valley automatic multiple-operant conditioning chambers to avoid a 2.0 mA electric shock that would last for 0.75 second, or terminate sooner if the rat lever became activated during the shock. In these tests, lever presses postponed the onset of shock for an initial period of 30 second, while only 10 seconds elapsed between shocks if no intervening response was elicited. The rats were run for a 40-minute control period before receiving the drug and then for approximately 2.5 hours after each treatment. Trans-d-N-methyl-4-phenyl-1,2,3,4-tetrahydro-1-naphthylamine hydrochloride was administered intraperitoneally both at 5 mg./kg. and at 10 mg./kg., respectively.

In four out of these eight so-called non-discriminated (Sidman) avoidance behavior rats, trans-d-N-methyl-4-phenyl-1,2,3,4-tetrahydro-1-naphthylamine hydrochloride was found to produce a moderate to marked increase in response rates. In these particular animals, the rates increased 2-6 times over their normal pre-drug control levels. On the other hand, in two other rats, the rates increased to about 1.5 times over their pre-drug control levels. The drug effect started within the first 20 minutes and was observed to continue for approximately one and a half hours after administration.

EXAMPLE XVIII

The 1-amino-4-phenyltetraline final products of Examples III-IX were tested for antidepressant activity by measuring their ability to reverse reserpine-induced hypothermia in the mouse according to the procedure described by B.M. Askew in *Life Science*, Vol. 2, p. 725 (1963). In this test, all the animals were individually housed in plastic chambers with a cardboard bottom. The mice were injected with reserpine subcutaneously at 2 mg./kg. and retained at an ambient temperature of 20° C. for a period of 18 hours. At this point, their rectal temperatures were initially ascertained and immediately thereafter they were divided into groups of 5-20 animals for testing purposes. Each group then received either saline as a control or the compound to be tested at a dose level of 32 mg/kg., administered intraperitoneally, and the resulting rectal temperatures were measured 2 hours later. In the table below, the entries are reported as mean rectal temperatures for each compound at the 2-hour mark, together with the number of animals tested in each particular group. In 20 reserpine-pretreated control mice that had been given the saline solution alone, the mean rectal temperature was found to be 25.1° ± 3.2° C.

| 1-Amino-4-Phenyltetralin Cpd. | Mean Rectal Temperature Temp. (° C.) ±S.D. | No. Rats |
|---|---|---|
| Trans-d-isomer of Example III | 34.1 ± 0.7 | (5) |
| Trans-l-isomer of Example III | 27.5 ± 2.9 | (5) |
| Trans-isomer of Example IV | 33.5 ± 1.5 | (20) |
| Cis-isomer of Example IV | 27.0 ± 3.4 | (5) |
| Trans-isomer of Example V | 33.5 ± 0.9 | (5) |
| Cis-isomer of Example V | 28.0 ± 2.3 | (5) |
| Trans-isomer of Example VI | 32.6 ± 0.7 | (5) |
| Cis-isomer of Example VI | 27.3 ± 3.6 | (5) |
| Trans-isomer of Example VII | 32.6 ± 0.7 | (5) |
| Cis-isomer of Example VII | 25.3 ± 4.4 | (5) |
| Trans-isomer of Example VIII | 33.5 ± 1.4 | (5) |
| Cis-isomer of Example VIII | 31.4 ± 2.4 | (5) |
| Trans-isomer of Example IX | 31.8 ± 2.5 | (10) |

| 1-Amino-4-Phenyltetralin Cpd. | Mean Rectal Temperature Temp. (° C.) ±S.D. No. Rats |
|---|---|
| Cis-isomer of Example IX | 30.8 ± 2.6 (10) |

EXAMPLE XIX

The 1-amino-4-phenyltetralin final products of Examples IV-V and VIII-IX were tested for antidepressant activity by measuring their ability to block tritium-labeled norepinephrine ($H^3NE$) uptake into the rat heart in vivo. For these particular studies, rats in groups of five were pretreated with the control vehicle or the drug to be administered at 32 μmoles/kg. (8.8 mg./kg.), via the intraperitoneal route, followed 20 minutes later by intravenous injection of dl-$H^3NE$ (having a specific activity of 9.5 c/mmole) at a dose level of 5 μc/kg. The rats were then sacrificed one hour ater administration of said agent ($H^3NE$), and the norepinephrine (NE) content present in the heart was subsequently isolated therefrom by means of extraction with alumina, followed by repeated elution of said alumina extracts with 0.05N aqueous hydrochloric acid. The specific activity (cpm/μg.) of $H^3NE$ in the heart was then determined by measuring the amount of radioactivity (using a liquid scintillation counter) and the NE content (fluorimetrically via an Auto-Analyzer of the type manufactured by the Technicon Instruments Corporation of Chauncey, N.Y.) of the aforesaid aqueous eluates. The results obtained in this manner are presented below in the following table, where the individual entries are each made from a separate experiment and constitute mean relative specific activities expressed in terms of percent control:

| 1-Amino-4-phenyltetralin Cpd. | Sp. Activity of Heart $H^3NE$ (% Control) |
|---|---|
| Trans-isomer of Example IV | 14, 19, 21, 25 |
| Cis-isomer of Example IV | 87, 104 |
| Trans-isomer of Example V | 71, 75 |
| Cis-isomer of Example V | 144 |
| Trans-isomer of Example VIII | 49, 49 |

| 1-Amino-4-phenyltetralin Cpd. | Sp. Activity of Heart $H^3NE$ (% Control) |
|---|---|
| Cis-isomer of Example VIII | 120 |
| Trans-isomer of Example IX | 60, 66 |
| Cis-isomer of Example IX | 93 |

What is claimed is:

1. A method for combating depression in the treatment of a mentally-depressed subject, which comprises administering to said subject an effective amount of a compound selected from the group consisting of the trans-isomers of 1-amino-4-phenyltetraline bases of the formula;

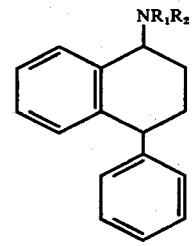

and the pharmaceutically acceptable acid addition salts thereof, wherein $R_1$ is a member selected from the group consisting of hydrogen and alkyl having from one to three carbon atoms, and $R_2$ is a member selected from the group consisting of hydrogen alkyl having from one to three carbon atoms and cycloalkyl having from three to six carbon atoms, said $R_2$ only being cycloalkyl when $R_1$ is hydrogen.

2. The method as claimed in claim 1 wherein the compound administered is trans-dl-N-methyl-4-phenyl-1,2,3,4-tetrahydro-1-naphthylamine.

3. The method as claimed in claim 1 wherein the compound administered is trans-d-N-methyl-4-phenyl-1,2,3,4-tetrahydro-1-naphthylamine.

4. The method as claimed in claim 1 wherein the compound administered is trans-dl-N-ethyl-4-phenyl-1,2,3,4-tetrahydro-1-naphthylamine.

5. The method as claimed in claim 1 wherein the compound administered is trans-dl-N,N-dimethyl-4-phenyl-1,2,3,4-tetrahydro-1-naphthylamine.

* * * * *